United States Patent
Kohlmann

(10) Patent No.: US 10,436,736 B2
(45) Date of Patent: Oct. 8, 2019

(54) MEASUREMENT DEVICE FOR MEASURING A PROPERTY OF A FLUID

(71) Applicant: Endress+ Hauser Conducta GmbH + Co. KG, Gerlingen (DE)

(72) Inventor: Frederick J. Kohlmann, Sussex, WI (US)

(73) Assignee: Endress+Hauser Conducta GmbH + Co. KG, Gerlingen (DE)

( * ) Notice: Subject to any disclaimer, the term of this patent is extended or adjusted under 35 U.S.C. 154(b) by 555 days.

(21) Appl. No.: 14/962,258

(22) Filed: Dec. 8, 2015

(65) Prior Publication Data

US 2017/0160222 A1    Jun. 8, 2017

(51) Int. Cl.
*G01N 27/30* (2006.01)
*G01N 27/414* (2006.01)
*G01N 27/28* (2006.01)

(52) U.S. Cl.
CPC ......... *G01N 27/302* (2013.01); *G01N 27/283* (2013.01); *G01N 27/414* (2013.01)

(58) Field of Classification Search
None
See application file for complete search history.

(56) References Cited

U.S. PATENT DOCUMENTS

| | | | | |
|---|---|---|---|---|
| 4,894,339 A | * | 1/1990 | Hanazato | C12N 11/08 204/403.1 |
| 5,016,201 A | * | 5/1991 | Bryan | G01N 27/4167 204/401 |
| 8,568,575 B2 | * | 10/2013 | Talutis | G01N 27/26 204/286.1 |
| 2011/0036913 A1 | * | 2/2011 | Merz | G01N 27/333 235/492 |
| 2011/0290045 A1 | * | 12/2011 | Hanko | G01N 27/333 73/866.5 |

FOREIGN PATENT DOCUMENTS

CN          1045183    *  9/1990    ......... G01N 27/416

* cited by examiner

*Primary Examiner* — Gurpreet Kaur
*Assistant Examiner* — Steven E Rosenwald
(74) *Attorney, Agent, or Firm* — Christopher R. Powers; PatServe

(57) ABSTRACT

A measurement device for measuring a property of a fluid, in particular a concentration of a substance or an ion concentration in said fluid or a pH-value of said fluid, comprising: a housing comprising a housing section to be immersed into the fluid during measurement operation, and an aperture foreseen in an outside wall of the housing section, in particular in a side wall surrounding an interior of the housing section or in a front wall closing off a front end of the housing section, for exposing a single sensor for measuring the property of the fluid to the fluid, when the housing section is immersed into the fluid. This allows quick and easy replacement of the single sensor and characterizes in that, a number of at least two sensors for measuring the property are foreseen, each of the sensors is mounted in a different outside surface region of a movable mechanical support, and the mechanical support is movably secured inside the housing by means allowing for the support to be transferred into a number of different measurement positions, wherein in each measurement position a different outside surface region of the support comprising one of the sensors is exposed to the aperture.

15 Claims, 5 Drawing Sheets

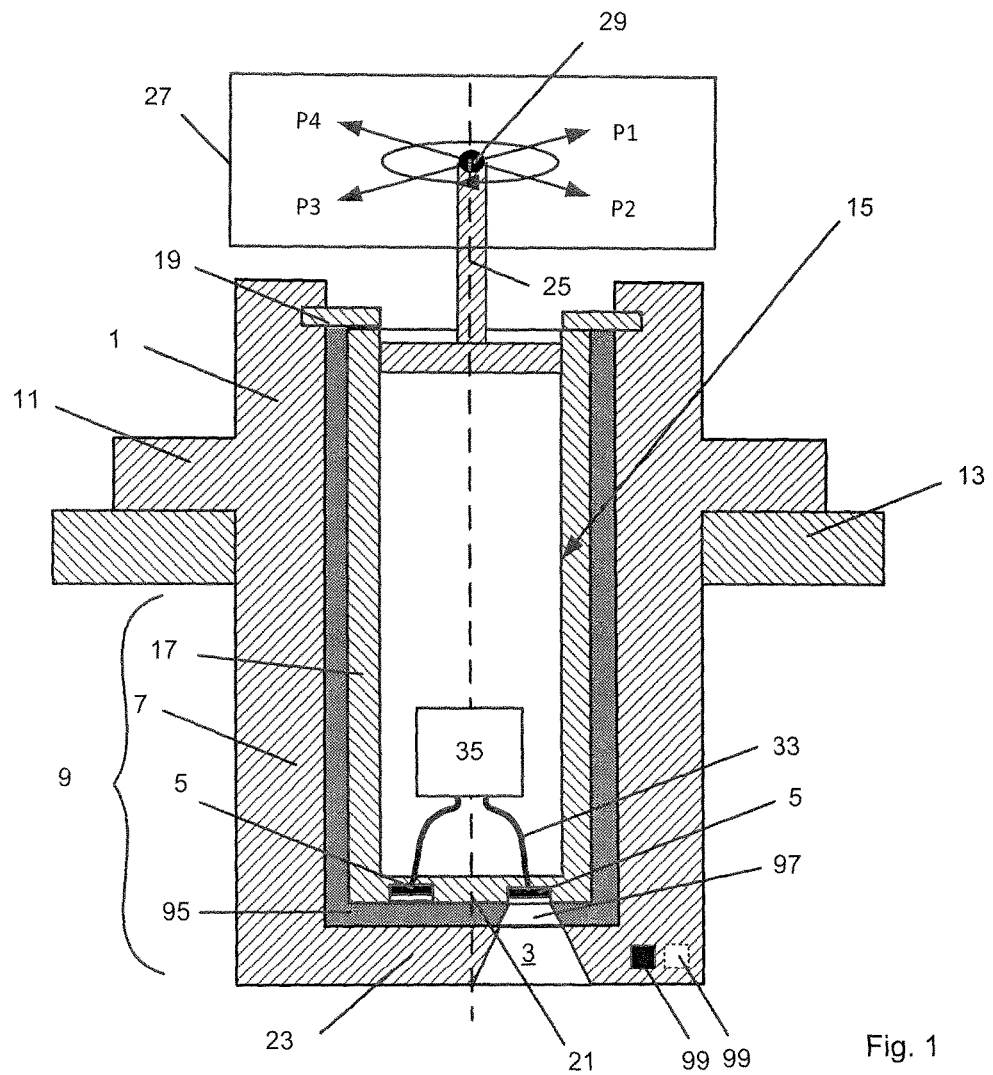
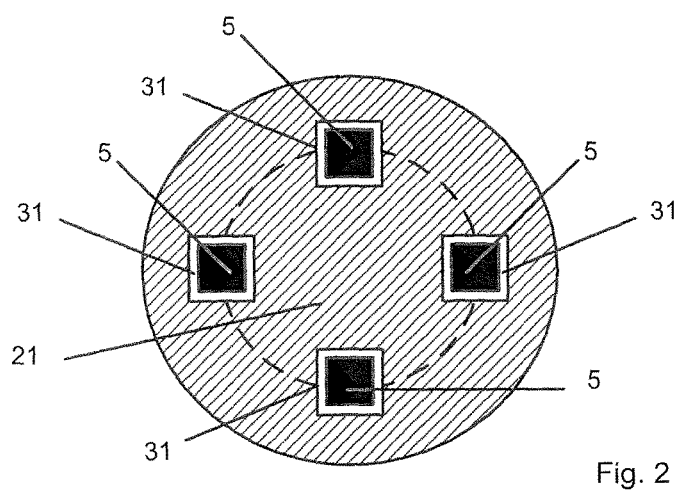
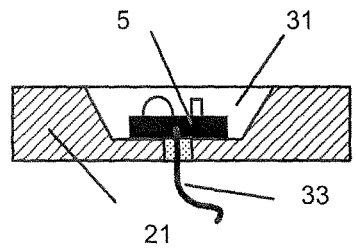
Fig. 1
Fig. 2
Fig. 3

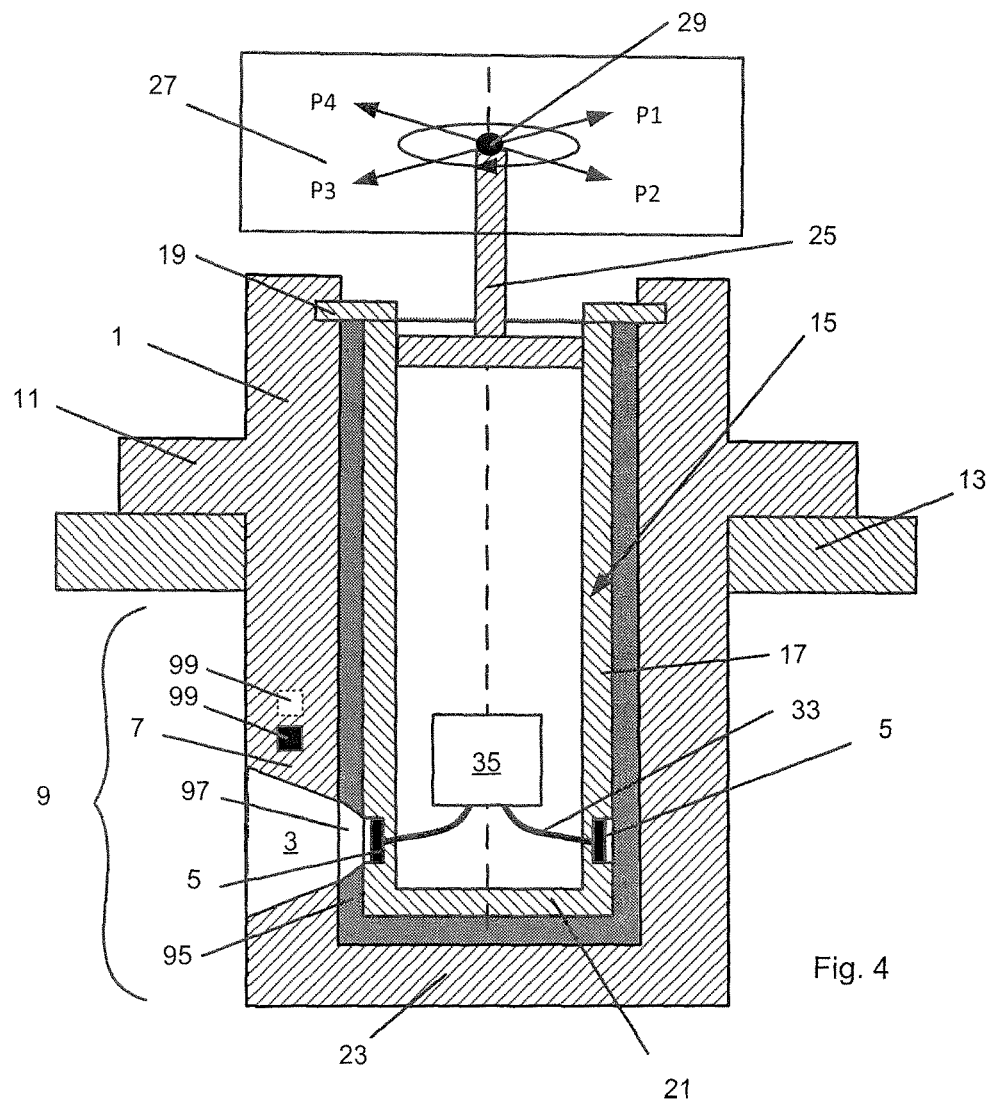
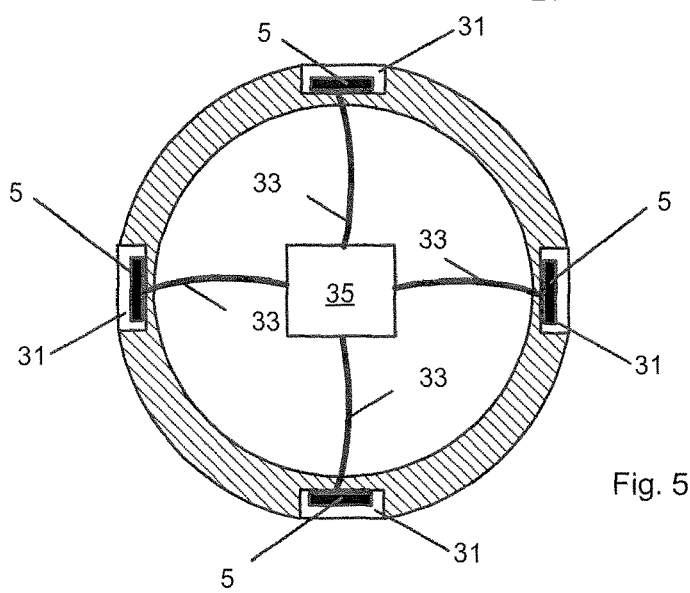

MEASUREMENT DEVICE FOR MEASURING A PROPERTY OF A FLUID

BACKGROUND AND SUMMARY OF THE INVENTION

The invention relates a measurement device for measuring a property of a fluid, in particular a concentration of a substance or an ion concentration in the fluid or a pH-value of the fluid, comprising a housing comprising a housing section to be immersed into the fluid during measurement operation and an aperture foreseen in an outside wall of the housing section, in particular in a side wall surrounding an interior of the housing section or in a front wall closing off a front end of the housing section, for exposing a single sensor for measuring the property of the fluid to the fluid, when said housing section is immersed into the fluid.

Measurement devices of this type are frequently used in laboratory measurements technology as well as in industrial process measurements technology in many fields of application, e.g. in chemistry, environmental analysis, biochemistry, biotechnology, pharmacy, food technology and water management.

These measurement devices comprise a single sensor capable of measuring the property required in the specific application, e.g. an electrochemical sensor, e.g. a potentiometric or an amperometric sensor, for determining a concentration of a certain substance or an ion concentration in the fluid or a pH-value of the fluid.

For these measurement devices, it is known in the art, to mount the sensor on an outside surface region of a mechanical support, which is inserted into a housing section of a housing to be immersed into the fluid during measurement and to provide an aperture in an outside wall of the housing section, through which the sensor is exposed to the fluid when the housing section is immersed into the fluid.

Unfortunately sensors, in particular electrochemical sensors, are sensitive elements frequently requiring replacement, re-calibration and/or cleaning. Replacement can e.g. be required due to damage of sensor components like e.g. ion-sensitive membranes, glass domes or glass bulbs of measurement cells of the sensor, occurring due to process conditions or due to operator induced strains the sensor is exposed to. Re-calibration is quite often performed periodically in order to ensure that the sensor is compliant to a measurement accuracy specified for it. It is e.g. applied in order to compensate for drifts of an offset of the sensor and/or changes of the span of the sensor, which may e.g. occur due to aging or wear of components of the sensor exposed to the fluid. Frequent cleaning is e.g. required in applications, where the sensor is likely to become soiled, coated and/or contaminated due to process conditions it is exposed to.

Each time replacement, re-calibration or cleaning is required the mechanical support carrying the sensor has to be taken out of the housing in order to enable the operator to replace the sensor or to transfer it to a treatment site, where it can be cleaned and/or calibrated. This is a time and cost intensive procedure, which quite often requires an interruption of an ongoing process performed at the measurement site.

In U.S. Pat. No. 9,146,138 B2 a measurement device for measuring a property of a fluid is described, comprising:
a housing comprising a housing section to be immersed into the fluid during measurement operation, and
an aperture foreseen in an outside wall of the housing section, in particular in a side wall surrounding an interior of the housing section or in a front wall closing off a front end of the housing section, for exposing a single sensor for measuring the property of the fluid to the fluid, when the housing section is immersed into the fluid.

The measurement device comprises a single sensor, which is mounted on a movable mechanical support movably secured inside the housing section by means allowing for the mechanical support to be moved into a measurement position, wherein the sensor is exposed to fluid entering the aperture and into a treatment position, wherein the sensor is facing a recess located in an inside wall of the housing. The recess is closed off by an outside surface of the support and is filled with a rinsing and/or calibration fluid. During normal operation, the support is kept in its measurement position. Whenever re-calibration or cleaning is required, the support is transferred into its treatment position, allowing for the sensor to be cleaned or re-calibrated on site. This has the advantage that the support carrying the sensor only needs to be taken out of the housing in case the sensor or the rinsing and/or calibration fluid needs to be replaced.

Nonetheless, the operating time, during which this device can be operated without any need for an ongoing process to be interrupted, is still limited to a time span given by the time between consecutive replacements of the sensor and/or the rinsing and/or calibration fluid.

Whereas re-calibrations of the sensor can be scheduled based on predetermined calibration time intervals, replacements of the sensor may become necessary at unexpected times. In this case the time required to perform the replacement as well as an interruption of an ongoing process required to perform the replacement may cause additional costs and severe inconveniences for the operator.

It is an object of the invention to provide a measurement device, allowing for quick and easy replacement of its sensor.

To this extent, the invention comprises a measurement device for measuring a property of a fluid, in particular a concentration of a substance or an ion concentration in said fluid or a pH-value of said fluid, comprising:
  a housing comprising a housing section to be immersed into the fluid during measurement operation, and
  an aperture foreseen in an outside wall of the housing section, in particular in a side wall surrounding an interior of the housing section or in a front wall closing off a front end of the housing section, for exposing a single sensor for measuring the property of the fluid to the fluid, when the housing section is immersed into the fluid, wherein according to the invention
  a number of least two sensors for measuring the property are foreseen,
  each of the sensors is mounted in a different outside surface region of a movable mechanical support, and
  said mechanical support is movably secured inside the housing by means allowing for the support to be transferred into a number of different measurement positions, wherein in each measurement position a different outside surface region of the support comprising one of the sensors is exposed to the aperture.

The invention further comprises a first refinement of the measurement device, wherein each of the sensors is located inside a recess foreseen in the corresponding outer surface region of the support, in particular a recess comprising a depth which is dimensioned such that the sensor does not extend beyond a frontline defined by an outside surface of said support surrounding the recess.

The invention further comprises a second refinement, wherein the means allowing for the support to be transferred into the predefined measurement positions comprise:

means allowing for the support to be transferred manually, in particular means comprising a ratcheting mechanism interlockingly engaging the support every time one of the measurement positions is reached, or a drive, in particular an electric motor or solenoid, for transferring the support into the predefined measurement positions, in particular a drive transferring the support from one measurement position into a consecutive measurement position each time it is activated, or a ratcheting mechanism for transferring the support into the predefined measurement positions, in particular a ratcheting mechanism transferring the support from one measurement position into a consecutive measurement position each time it is activated.

The invention further comprises a third refinement, wherein said support comprises a cylindrical section, which is rotatably secured inside a cylindrical interior of said housing section by securing means, in particular a retaining ring, allowing for said support to be transferred into said different measurement positions by rotating said cylindrical section around its longitudinal axis, and either said sensors are arranged in a circle on outer surface regions of a front wall of said cylindrical section resting on said front wall of said housing section, wherein said aperture is foreseen in an off-centered position in said front wall corresponding to the positions of said sensors on said front wall of said support, or said sensors are arranged in a circle on outer surface regions of a cylindrical wall of said cylindrical section surrounded by said side wall of said housing section, wherein said aperture is foreseen in said side wall at a height corresponding to the height of said sensors on said cylindrical section of said support.

The invention further comprises a fourth refinement, wherein said mechanical support comprises a conveyor belt, in particular a conveyor belt comprising two to side sections extending in a direction essentially parallel to a longitudinal axis of said housing section along opposing inside surfaces of said housing section and one or two connecting sections connecting the two side sections, said sensors are mounted on outside surface regions, in particular in recesses foreseen in said outside surface regions, distributed along a length of said conveyor belt, and said means allowing for the support to be transferred into said predefined measurement positions comprise conveying means allowing for the support to be transferred into said different measurement positions by conveying the conveyor belt, such that in each measurement position a different sensor located in one of said outside surface regions of said conveyor belt is exposed said aperture.

According to a first preferred embodiment of the fourth refinement, said aperture is located in said front wall of said housing section and said conveyor belt comprise an essentially flat region, larger than the size of said sensors, abutting on a flat inside surface of a front wall of said housing section surrounding said aperture, or said aperture is located in said side wall of said housing section and said conveyor belt comprises an essentially flat region, larger than the size of said sensors, abutting on a flat inside surface of said side wall of said housing section surrounding said aperture.

According to a second preferred embodiment of the fourth refinement, said conveyor belt is mounted on a mounting frame, in particular a mounting frame equipped with ball bearings allowing for said conveyor belt to be rolled along the mounting frame, in particular a mounting frame supporting outer rims of said conveyor belt.

According to a third preferred embodiment of the fourth refinement, said conveyor belt forms a closed loop, comprising two to side sections extending in a direction essentially parallel to the longitudinal axis of the housing section along opposing inside surfaces of the housing section and two connecting section connecting the two side sections completing the closed loop, and said means allowing for the support to be transferred into the different measurement positions comprise:

an opening in said housing for exposing a section of said conveyor belt allowing for the conveyor belt to be conveyed manually, or conveying means, in particular one or two toothed wheels comprising teeth successively engaging and disengaging into a section, in particular one of said connecting sections, in particular an outer rim of said connecting section, of said conveyor belt, when said conveyor belt is conveyed forward, allowing for the conveyor belt to be conveyed manually or comprising a drive, in particular a drive turning at least one of said wheels, in particular a drive set up to convey the conveyor belt from one measurement position into a consecutive measurement position each time it is activated.

According to a fourth preferred embodiment of the fourth refinement, said means allowing for the support to be transferred into said different measurement positions comprise a ratcheting mechanism engaging a section of said conveyor belt, in particular a section extending into a housing section adjacent to said housing section to be immersed into said fluid, in particular a ratcheting mechanism designed to convey said conveyor belt forward by distance corresponding to a distance between consecutive sensors on said outer surface regions of said conveyor belt each time it is activated, in particular a ratcheting mechanism designed to be activated manually, in particular via a lever or a push button, or via an electrical signal.

According to a fifth preferred embodiment of the fourth refinement, said conveyor belt comprises connecting means foreseen at its opposite ends allowing for the conveyor belt to be connected to a replacement conveyor belt of identical design.

According to a sixth preferred embodiment of the fourth refinement, said sensors comprise a mechanically rigid base and are mounted directly onto a surface, in particular a surface of a recess foreseen in the respective outside surface regions of the conveyor belt, or said sensors are mounted on mechanically rigid elements, e.g. ceramic discs, foreseen at the respective outside surface regions of said conveyor belt, or reinforcements reinforcing the sections of said conveyor belt comprising said sensors are foreseen.

The invention further comprises preferred embodiments, wherein
- said sensors are calibrated sensors, which were calibrated before said measurement device is put into measurement operation, and/or
- said sensors are electrochemical sensors, in particular potentiometric or amperometric sensors, in particular electrochemical sensors comprising an analyte sensitive component, in particular membrane or a semiconductor-element, in particular a semiconductor-element comprising an Electrolyte-Insulator-Semiconductor structure, in particular an ion sensitive field effect transistor (ISFET) or a capacitor, whose capacitance depends on the concentration of the substance to be determined.

The invention further comprises preferred embodiments, wherein
- all of said sensors are permanently connected to a measurement electronics via connecting lines, or
- each of said sensors comprises a sensor module allowing for said sensor to be powered and for its measurement results to be transferred wirelessly, or
- each sensor is connected to a contact and only the sensor exposed to said aperture is connected to a measurement electronics via a contact mounted inside said housing section and connected to said measurement electronics, which is pressed against the contact connected to said sensor, when said support is transferred into the measurement position, wherein said sensor is exposed to said aperture.

The invention further comprises a fifth refinement, wherein
- at least one temperature sensor, in particular a thermo element, for measuring a temperature prevailing at a measurement site is foreseen, in particular a temperature sensor, which is located near said aperture, in particular a temperature sensor, which is mounted independently of the support carrying said sensors, and
- said temperature sensor is connected to a measurement electronics designed to perform temperature compensations of temperature dependent measurement errors of measurement results obtained by said sensors.

The invention further comprises a sixth refinement, wherein sealing means are foreseen, providing a seal between said aperture and an interior of said housing section, in particular sealing means provided by:
- at least one surface of said support, in particular a surface of a cylindrical section or surfaces of sections of a conveyor belt of said support, surrounding said sensors, sealing by abutting on an inner surface of said housing section surrounding said aperture, or
- a sealing element filling a gap between said support and said housing section and comprising an opening located adjacent to said aperture.

It is an advantage of the invention, that the sensor performing the measurements can be easily replaced by a new one simply by transferring the support into the next measurement position. This way, the operating time, during which this device can be operated without any need for an ongoing process to be interrupted, is much longer than the time span a single sensor can be operated for before it requires cleaning, recalibration or replacement.

The invention and further advantages are explained in more detail using the figures of the drawing, in which four exemplary embodiments are shown.

BRIEF DESCRIPTION OF THE DRAWING

FIG. 1 shows: a measurement device comprising sensors mounted on a front surface of a rotatable mechanical support;

FIG. 2 shows: a view of the front surface of the mechanical support of FIG. 1;

FIG. 3 shows: a cross sectional view of a section of the front wall of the mechanical support of FIG. 1 comprising one of the sensors;

FIG. 4 shows: a measurement device comprising sensors mounted on a side wall of a rotatable mechanical support;

FIG. 5 shows: a cross sectional view of the side wall of the mechanical support of FIG. 4;

DETAILED DISCUSSION IN CONJUNCTION WITH THE DRAWINGS

Figure 6:
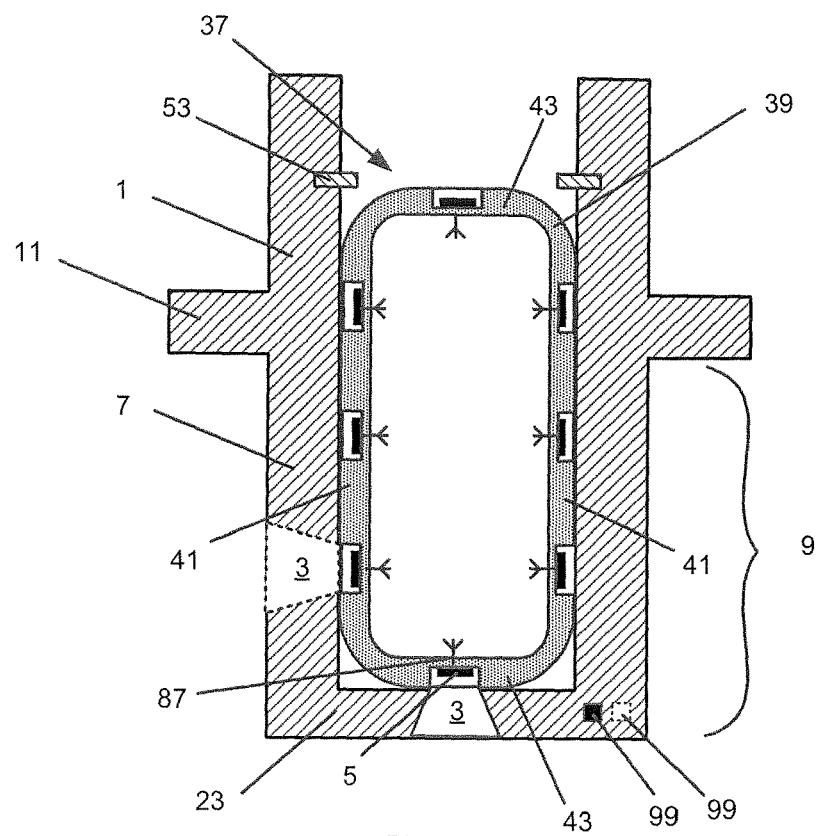
FIG. 6 shows: a measurement device comprising sensors on a conveyor belt.

The invention concerns a measurement device for measuring a property of a fluid, in particular a concentration of a substance or an ion concentration in said fluid or a pH-value of said fluid, comprising a housing comprising a housing section to be immersed into the fluid during measurement operation and an aperture foreseen in an outside wall of said housing section for exposing a single sensor for measuring the property of the fluid to the fluid, when the housing section is immersed into the fluid.

According to the invention a number of least two, preferably more, sensors for measuring the property are foreseen. Each of the sensors is mounted in a different outside surface region of a movable mechanical support. In addition, the mechanical support is movably secured inside the housing by means allowing for the support to be transferred into a number of different measurement positions, corresponding to the number of sensors foreseen on the support, wherein in each measurement position a different outside surface region carrying one of the sensors is exposed to the aperture.

When put into operation, the support will take up a first measurement position, wherein the measurements are performed by the sensor exposed to the aperture in this first measurement position. Every time the sensor performing the measurements will require cleaning, re-calibration and/or replacement, the support will be transferred into a consecutive next measurement position, exposing the next sensor in line to the fluid entering the aperture. Exchanging the sensor by the next one in line foreseen on the support does not require the support to be taken out of the housing. Sensor exchanges can thus be performed very quickly and do not require any interruption of an ongoing process performed on the measurement site.

To this extent, any type, shape and/or design of the mechanical support can be used, which can be movably secured inside the housing such that it can be transferred into different measurement positions, wherein in each measurement position a different outside surface region of the support equipped with one of the sensors is exposed to the aperture. Four embodiments are shown in the figures and are described in detail below. The invention is however not limited to the embodiments shown. Other types, shapes and/or designs of the support and/or other means allowing for the support to be transferred into at least two different predefined measurement positions can be applied instead.

All embodiments shown comprise a housing 1, comprising an aperture 3 designed to expose a single sensor 5 capable of measuring the property of the fluid to the fluid. In each embodiment the aperture 3 is foreseen in an outside wall of a housing section 9 of the housing 1, to be immersed into the fluid during measurement operation, e.g. in a side wall 7 surrounding an interior of the housing section 9 or in a front wall 23 closing off a front end of the housing section 9. The housing 1 is preferably equipped with mounting means 11 for mounting the housing 1 at a measurement site, such that the housing section 9 forms a probe extending into the fluid foreseen at the measurement site. The mounting means 11 can e.g. comprise a flange, to be mounted on a corresponding counter flange 13 foreseen at the measurement site. Obviously other types of mounting means known to the person skilled in the art can be applied.

FIGS. 1 and 4 show two embodiments of a measurement device according to the invention, wherein the support 15 comprises a cylindrical section 17, which is secured inside a cylindrical interior of the housing section 9 by a securing means 19, for example a retaining ring, allowing for the cylindrical section 17 of the support 15 to be rotated around its longitudinal axis. The cylindrical section 17 is closed off on its front end by a front wall 21 resting on the front wall 23 of the housing 1 closing off the cylindrical interior of the housing section 9.

Rotation of the cylindrical section 17 can either be induced by exerting a rotational force on the cylindrical section 17 itself or on an extension 25 attached to the cylindrical section 17. The latter version is shown in FIGS. 1 and 4. Rotation can e.g. be performed manually by the operator. In this case the cylindrical section 17 or the extension 25 attached to it has to extend to the outside of the housing 1 to be accessible to the operator. Alternatively, rotation can be performed automatically by a drive 27 only schematically shown in FIGS. 1 and 4, e.g. an electric motor or solenoid, foreseen inside the housing 1 for turning the cylindrical section 17 or the extension 25. In the latter case rotation can e.g. be triggered by manually pressing a button foreseen on the outside of the measurement device or via an electrical signal sent to the drive 27.

In addition means 29 schematically shown in FIGS. 1 and 4 are foreseen, allowing for the support 15 to be transferred into a number of predefined measurement positions Pj:=P1, P2, P3, P4 by turning it around its longitudinal axis. In case rotation is performed manually, the means 29 preferably comprise a ratcheting mechanism, interlockingly engaging the support 15, e.g. by engaging the cylindrical section 17 or the extension 25, every time one of the measurement positions Pj is reached. In case rotation is performed by the drive 27, the drive 27 is preferably set up to turn the cylindrical section 17 either directly or via turning of the extension 25 by a predefined angle of rotation corresponding to the angle of rotation required to transfer the support 15 from one measurement position Pj to the next each time it is activated.

In the embodiment shown in FIG. 1, the sensors 5 are arranged in a circle in outer surface regions of the front wall 21 of the cylindrical section 17 resting on the front wall 23 of the housing section 9. FIG. 2 shows a front view of the front wall 21 including four sensors 5 equidistantly distributed along the circle. Each sensor 5 is preferably located inside a recess 31 foreseen in the corresponding outer surface region of the front wall 21. The depth of the recesses 31 is preferably dimensioned such that the sensors 5 do not extend beyond a frontline defined by the outside surface of the front wall 21 surrounding the respective recess 31. FIG. 3 shows a cross sectional view of one of the sensors 5 of FIGS. 1 and 2 inserted in one of the recesses 31 in the front wall 21 of the support 15, as well as a connecting line 33 for connecting the sensor 5 to a measurement electronics 35. In this embodiment the aperture 3 foreseen for exposing a single sensor 5 to the fluid in each of the measurement positions Pj is located in an off-centered position in the front wall 23 of the housing section 9, corresponding to the positions of the sensors 5 on the front wall 21 of the support 15.

The embodiment shown in FIG. 4 differs from the embodiment shown in FIG. 1 in that the sensors 5 are arranged in a circle in outer surface regions of a cylindrical wall of the cylindrical section 17 of the support 15. FIG. 5 shows a cross sectional view of the support 15 at the height of the sensors 5. Again, the sensors 5 are preferably mounted in recesses 31 foreseen in the respective outside surface regions of the cylindrical section 17. Here, the aperture 3 foreseen for exposing a single sensor 5 to the fluid in each of the measurement positions Pj is located in the side wall 7 of the housing section 9 at a height corresponding to the height of the sensors 5 on the cylindrical section 17 of the support 15.

In both embodiments, the number of sensors 5, which can be foreseen, is limited by the size of the diameter of the housing section 9, which in turn limits the diameter of the cylindrical section 17 of the support 15 in relation to the given size of the sensors 5. A larger diameter of the housing section 9 requires a larger diameter of the opening foreseen at the measurement site, through which the housing section 9 is to be immersed into the fluid. In consequence, the number of sensors 5 limiting the operating time of the device is limited by the size of the diameter of the opening foreseen at the measurement site.

In order to further enhance the number of sensors 5 and thus the operating time of the device, measurement devices according to the invention can be equipped with a mechanical support comprising a conveyor belt. In this case, the sensors 5 are mounted in outside surface regions distributed along a length of the conveyor belt and the means allowing for the support to be transferred into the different measurement positions Pj comprise conveying means allowing for the support to be transferred into said different measurement positions Pj by conveying the conveyor belt, such that in each measurement position Pj a different sensor 5 is exposed to the aperture 3 foreseen in the outside wall of the housing section 9 to be immersed into the fluid.

Figure 7:
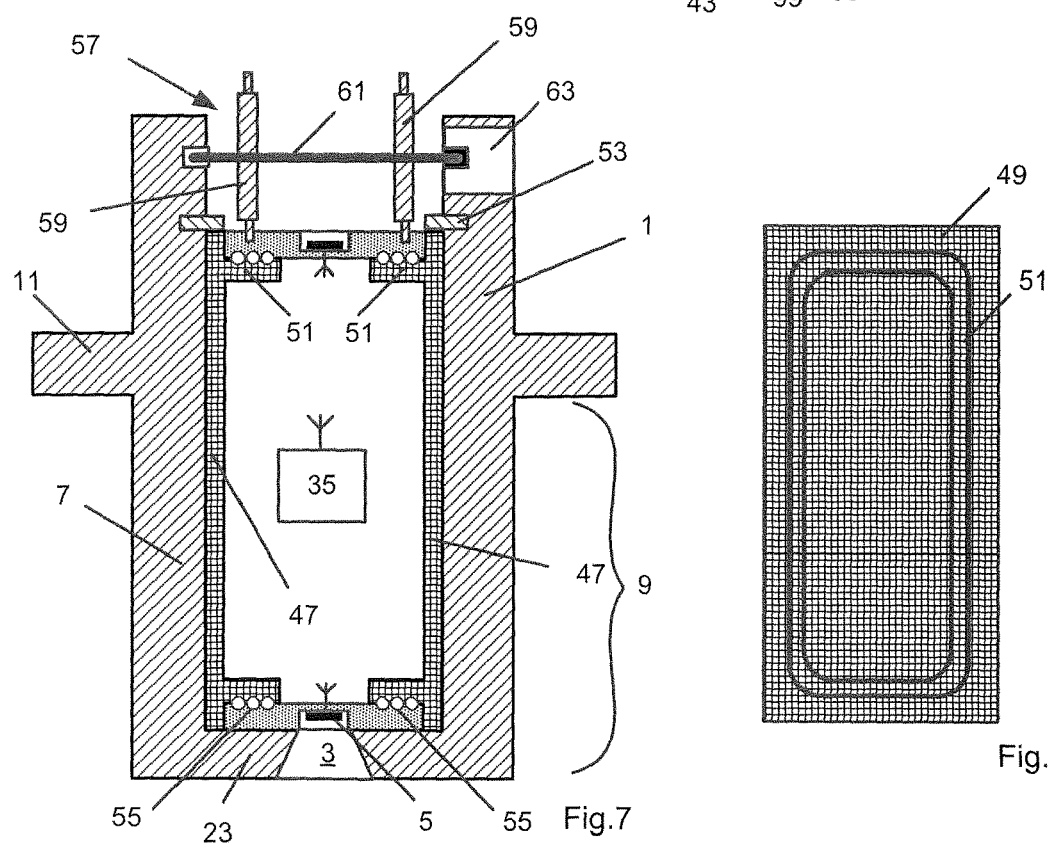
FIG. 7 shows: a cross sectional view of the device of FIG. 6 in a cross sectional plane perpendicular to the plane shown in FIG. 6.

FIG. 6 shows a first embodiment of a measurement device comprising mechanical support 37 comprising a conveyor belt 39. In this embodiment, the conveyor belt 39 forms a closed loop, comprising two side sections 41 extending in a direction essentially parallel to the longitudinal axis of the housing section 9 along opposing inside surfaces of the housing section 9 and two connecting sections 43 connecting the two side sections 41 to form a closed loop. FIG. 7 shows a cross sectional view of the measurement device of FIG. 6 in a plane perpendicular to the cross sectional plane shown in FIG. 6. Like in the previous embodiments, the aperture 3 for exposing a single sensor 5 to the fluid can e.g. be located in the front wall 23 of the housing 1 closing off the front end of the housing section 9 as shown in FIG. 6 or in the side wall 7 of the housing section 9 as indicated by dotted lines in FIG. 6. In the first case, the conveyor belt 39 is mounted inside the housing section 9, such that the connecting sections 43 comprise an essentially flat region, larger than the size of the sensors 5, abutting on a flat inside surface of the front wall 23 of the housing section 9 surrounding the aperture 3. In the second case, the conveyor belt 39 is mounted inside the housing section 9, such that at least one of the side sections 41 comprises an essentially flat region, larger than the size of the sensors 5, abutting on a flat inside surface of the side wall of the housing section 9 surrounding the aperture 3.

In this embodiment, the interior of the housing section 9 preferably comprises a square or rectangular cross section, allowing for the outside surfaces of the essentially flat regions to be in close contact to the corresponding inside surfaces of the outside wall of the housing section 9.

Figure 8:
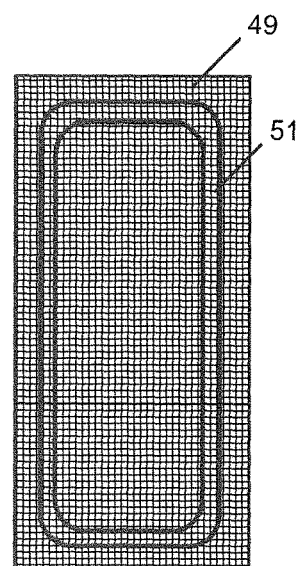
FIG. 8 shows: a front view of one of the insert of FIG. 6 and FIG. 7.

The conveyor belt 39 is preferably mounted on a mounting frame 45, supporting the conveyor belt 39 at least in a number of different positions sufficient to ensure a cross sectional shape of the conveyor belt 39 required in the first and/or the second case. In the embodiment shown the mounting frame 45 comprises two inserts 47. Each insert 47 comprises a base 49 extending in parallel to the longitudinal axis of the housing section 9 along opposing inside surfaces of the housing section 9 and a shoulder 51 extending in a direction perpendicular to the longitudinal axis of the housing section 9 into the interior thereof. FIG. 8 shows a view of a front of one of the inserts 47 facing towards the interior of the housing section 9. Each shoulder 51 supports an outer rim of the conveyor belt 39 in at least a number of positions sufficient to sustain the required shape of the conveyor belt 39. In the embodiment shown, each shoulder 51 forms a closed loop of a shape corresponding to the shape of the loop formed by the conveyor belt. 39. During production of the measurement device the inserts 47 are inserted on both sides of the loop shaped conveyor belt 39. Following this the conveyor belt 39 is inserted into the housing section 9 and secured in its position, e.g. by a retaining ring 53, holding the inserts 47 in place.

In this embodiment the support 37 is transferred from one measurement position into the next by conveying the conveyor belt 39 forward along the mounting frame 45 by a distance corresponding to the distance between consecutive sensors 5 on the belt. In order to reduce friction, the gliding surfaces of the conveyor belt 39 and the mounting frame 45 are preferably smooth surfaces exhibiting a low gliding resistance. Alternatively, the shoulders 51 of the mounting frame 45 can be equipped with ball bearings 55 allowing for the conveyor belt 39 to be rolled along on the shoulders 51 supporting it.

In a very basic embodiment, conveyance of the conveyor belt 39 can be performed manually via an opening in the housing 1 exposing a section, e.g. the upper connecting section 43, of the conveyor belt 39. Alternatively, conveying means 57 can be foreseen for conveying the conveyor belt 39 forward. To this extent, conveying techniques for conveying conveyor belts applied in various fields of technology can be applied. In the embodiment shown in FIGS. 6 and 7 the conveying means 57 comprise at least one, preferably two toothed wheels 59 comprising teeth successively engaging and disengaging into the upper connecting section 43 of the conveyor belt 37 as the conveyor belt 37 is conveyed forward by the active rotation of at least one of the toothed wheels 59. In the embodiment shown two toothed wheels 59 are foreseen, which are mounted and spaced apart from each other on a common axis of rotation 61, such that each of them is in engagement with an outer rim of the conveyor belt 39. Here conveyance can be performed manually, e.g. by manually turning at least one of the toothed wheels 59 or the axis of rotation 61 attached thereto. If the conveyor belt 37 is to be conveyed manually, the conveying means preferably comprises a ratcheting mechanism interlockingly engaging the support 37, e.g. a clamp engaging a section of the conveyor belt 37 or a latch engaging at least one of the toothed wheels 59, every time one of the measurement positions Pj is reached. Alternatively a drive 63, e.g. an electric motor or solenoid can be foreseen for turning at least one of the toothed wheels 59 or the axis of rotation 61. Like in the previous embodiments, the drive 63, is preferably set up to turn the toothed wheels 59 by a predefined angle of rotation corresponding to the angle of rotation required to transfer the conveyor belt 39 from one measurement position Pj to the next one. Rotation can e.g. be triggered by pressing a button foreseen on the outside of the measurement device or via an electrical signal sent to the measurement device.

Figure 9:
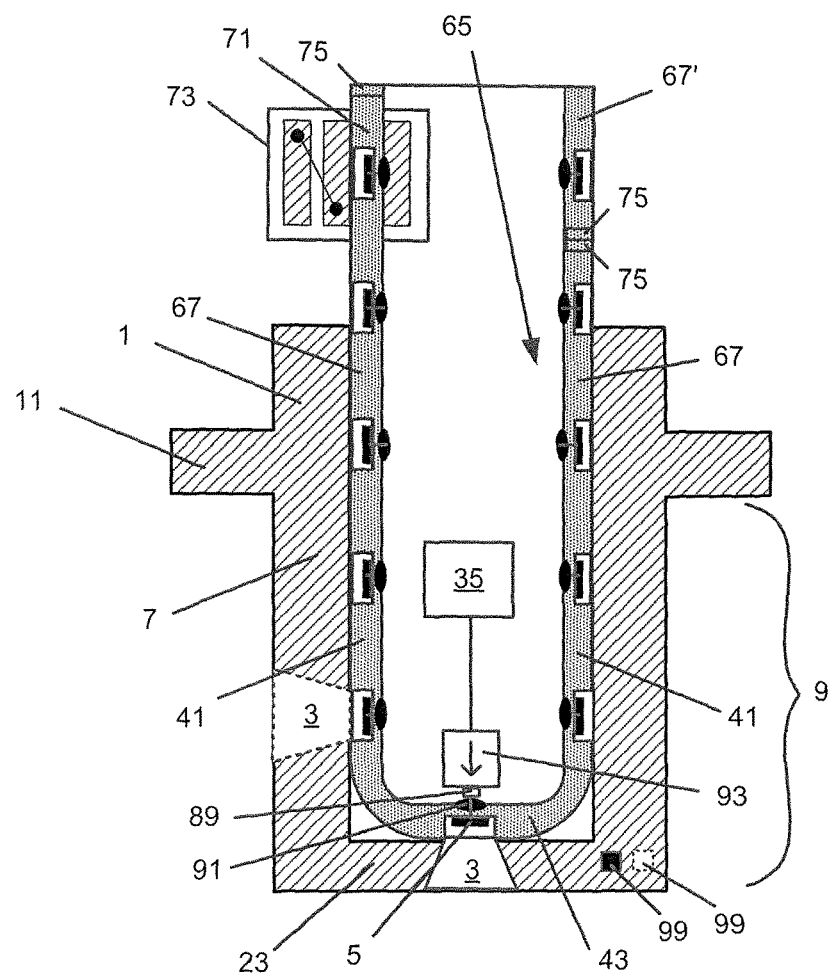
FIG. 9 shows: a measurement device comprising sensors on a conveyor belt.
Figure 10:
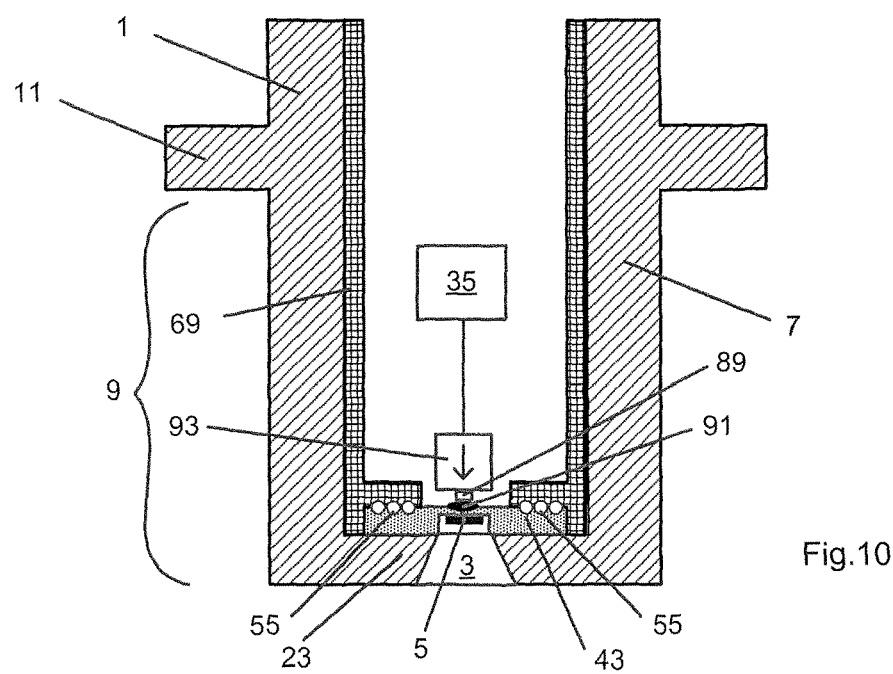
FIG. 10 shows: a cross sectional view of the device of FIG. 9 in a cross sectional plane perpendicular to the plane shown in FIG. 9.

FIG. 9 shows a further embodiment, wherein the support 65 comprises a conveyor belt 67 and wherein the sensors 5 are mounted on outside surface regions distributed along the length of the conveyor belt 67. FIG. 10 shows a cross sectional view of the device of FIG. 9 in a cross sectional plane perpendicular to the one shown in FIG. 9. Due to the great resemblance to the previously described embodiment only the existing differences are described in detail below. The embodiment shown in FIGS. 9 and 10 differs from the previously described embodiment in that the conveyor belt 67 forms an open loop, comprising two side sections 41 extending in a direction essentially parallel to the longitudinal axis of the housing section 9 along opposing inside surfaces of the housing section 9 and only one connecting section 43 connecting the two side sections 41 inside the housing section 9. Like in the previous embodiment, the conveyor belt 67 is preferably mounted on a mounting frame 69 ensuring the cross sectional shape required for it as described above, which if necessary can be equipped with ball bearings 55 to facilitate conveyance of the conveyor belt 67 on the mounting frame 69.

Conveyance of the conveyor belt 67 into the respective measurement positions Pj can be performed by exerting a pulling or a pushing force on a section 71 of the conveyor belt 67, preferably a section 71 extending into a section of the housing 1 adjacent to the housing section 9 to be immersed. This force is preferably provided by a ratcheting mechanism 73 only schematically shown in FIG. 9, engaging the section 71. The ratcheting mechanism 73 can be activated manually, e.g. by a lever or a push button, or by an electrical signal sent to it every time the sensor 5 needs to be replaced by the next one in line. The ratcheting mechanism 73 is preferably designed to pull or to push the conveyor belt 67 forward by distance corresponding to the distance between consecutive sensors 5 on the outer surface regions of the conveyor belt 67, each time it is activated.

In this embodiment the conveyor belt 67 preferable comprises connecting means 75 at its opposite ends allowing for the conveyor belt 67 to be connected to a replacement conveyor belt 67' of identical design. This has the advantage, that replacement conveyor belts 67' can be mounted on the device, e.g. via an opening the housing 1, exposing the end of the previously used belt, whilst the device remains installed at the measurement site and whilst a section of the previous conveyor belt 67 covering the aperture 3 is sealing off the interior of the housing section 9.

Figure 11:
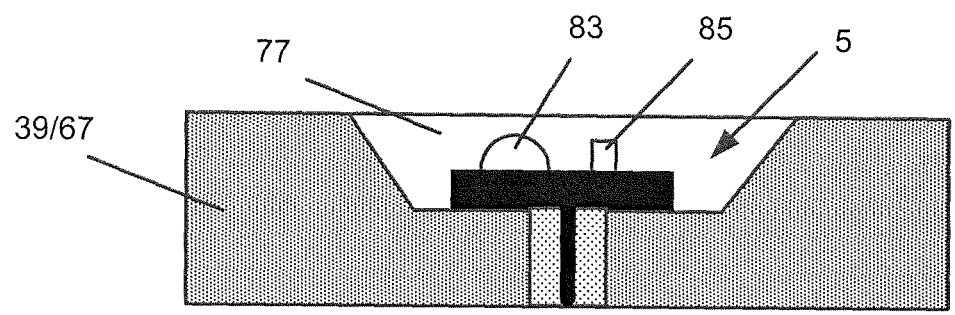
FIG. 11 shows: a sensor mounted in a recess of a conveyor belt.

Like in the previous embodiments shown in FIG. 1-5, the sensors 5 foreseen in the embodiments shown in FIG. 6-10 are preferably mounted in recesses 77 foreseen in the respective outside surface regions of the conveyor belt 39, 67. Sensors 5 comprising a mechanically rigid base can e.g. be mounted directly onto a surface inside the respective recess 77, as shown in FIG. 11. Sensors 5 lacking a rigid base are preferably mounted on mechanically rigid elements 79, e.g. ceramic discs, foreseen inside the recesses 77 as e.g. shown in FIG. 12.

Figure 13:
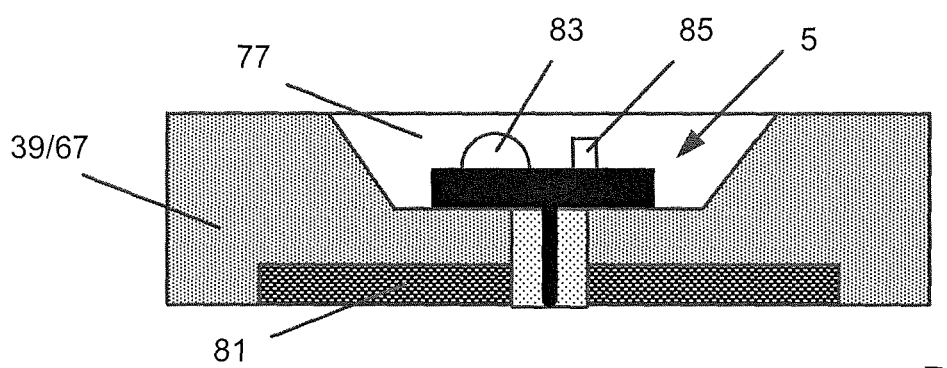
FIG. 13 shows: a reinforced section of a conveyor belt.

Alternatively, reinforcements 81 can be foreseen on the conveyor belt 39, 67 reinforcing the sections of the conveyor belt 39, 67 comprising the sensors 5, as e.g. shown in FIG. 13.

As already mentioned above, measurement devices according to the invention comprise sensors 5 capable of measuring the property of the fluid to be measured by the device. To this extent sensors known in the art can be applied. The sensors 5 can e.g. be electrochemical sensors, like for example potentiometric or amperometric sensors for determining concentrations of certain substances or ion concentrations in the fluid or a pH-value of the fluid.

Figure 12:
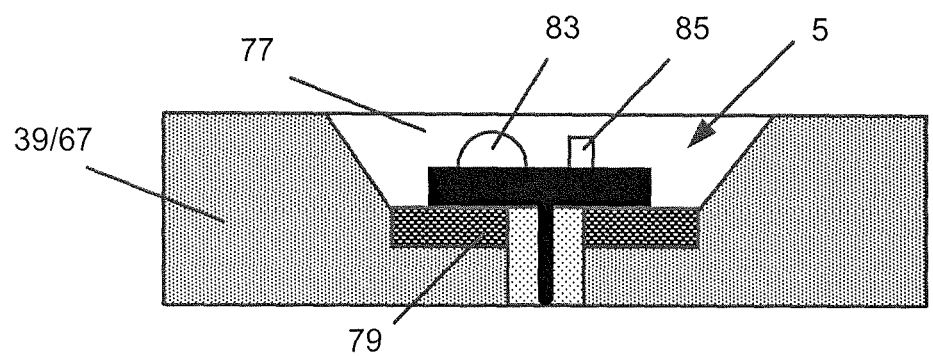
FIG. 12 shows: a sensor mounted on a rigid element in a recess of a conveyor belt.

Potentiometric sensors usually comprise a measuring half-cell 83 and a reference half-cell 85 schematically shown in FIG. 11-13. When in contact with the fluid, the measuring half-cell 83 provides an electric potential dependent on the concentration of the analyte in the fluid. At the same time, the reference half-cell 83 provides a reference-potential, which is essentially independent of the analyte concentration. With these sensors, the property to be measured is determined based on the potential difference between the measuring half-cell 83 and the reference half-cell 85. Amperometric sensors can e.g. comprise a three electrode circuit, comprising a working electrode, a counter electrode and a non-current carrying reference electrode.

Electrochemical sensors typically comprise an analyte sensitive component. The analyte sensitive component can e.g. be a membrane, e.g. a glass dome or bulb, e.g. a glass membrane sensitive to the concentration of the substance, e.g. the concentration of $H^+$ or $H_3O^+$ ions in the fluid, or a semiconductor-element. Semiconductor-elements suitable for this purpose comprise Electrolyte-Insulator-Semiconductor structures (EIS structures), like for example ion sensitive field effect transistors (ISFET) or capacitors, whose capacitance depends on the concentration of the substance to be determined.

Calibration of the sensors 5 can be performed individually, each time the support 15, 37, 65 is transferred into one of the measurement positions Pj by solely calibrating the sensor 5 facing the aperture 3 in the respective measurement position Pj. It is however much more advantageous to calibrate all sensors 5 foreseen on the support 15, 37, 65 before the measurement device is put into operation. To this extent, pre-calibrated sensors 5 can be installed on the support 15, 37, 65 as well as on replacement conveyor belts 67'. As an alternative all sensors 5 can be installed on the device and be calibrated one after the other by transferring the support 15, 37, 65 into the respective measurement positions Pj, allowing for the respective sensor 5 to be calibrated, before the device is put into measurement operation.

All sensors 5 can be permanently connected to the measurement electronics 35 via connecting lines 33, as is e.g. shown in FIGS. 1, 3, 4 and 5. In the embodiment shown in FIGS. 6 and 9 the connecting lines could e.g. be run along the back side of the conveyor belt 39, 67. Alternatively, the sensors 5 can be equipped with a sensor module allowing for the sensors 5 to be powered and their measurement results to be transferred wirelessly, as indicated by the antennas 87 shown in FIGS. 6 and 7.

Since during measurement operation, only the sensor 5 exposed to the aperture 3 is used, it is sufficient, if only the sensor 5 facing the aperture 3 at the time, is connected to the measurement electronics 35. The required electrical connection of the respective sensor 5 to the measurement electronics 35 is preferably provided by a contact 89, mounted inside the housing section 9 and connected the measurement electronics 35, which is pressed against a contact 91 connected to the sensor 5, e.g. by a spring 93 or leverage type of device, when the support 15, 37, 65 is transferred into the measurement position Pj, wherein the respective sensor 5 is facing the aperture 3, as shown in FIGS. 9 and 10.

Measurement devices according to the invention preferably comprise sealing means, providing a seal between the aperture 3 and the interior of the housing section 9. Depending on the embodiment chosen, the seal can e.g. be provided by a surface of the support 15, 37, 65, e.g. a surface of the cylindrical section 17 of the support 15 shown in FIGS. 1-5 or by surfaces of sections of conveyor belt 39, 67 surrounding the sensors 5 shown FIG. 6-10, sealing by abutting on an inner surface of the outside wall of the housing section 9 surrounding the aperture 3. Alternatively a sealing element 95 filling a gap between the support 15 and the housing section 9 and comprising an opening 97 located adjacent to the aperture 3, through which fluid entering the aperture 3 reaches the sensor 5 facing the aperture 3 at the time, can be foreseen, as shown in FIGS. 1 and 4.

Just like measurement devices known in the art, the measurement devices according to the invention are preferably equipped with a temperature sensor 99, e. g. a thermo element, for measuring the temperature prevailing at the measurement site. The temperature sensor 99 is preferably connected to the measurement electronics 35 of the device, which is preferably designed, to perform temperature compensations of temperature dependent measurement errors of the measurement results obtained by the sensors 5. The temperature sensor 99 is preferably located near the aperture 3 foreseen in the housing section 9. In addition, it is preferably mounted independently of the support 15, 37, 65, carrying the sensors 5. Here it is an advantage of the invention, that the temperature sensors 99 does not have to be removed from its position, when the sensor 5 performing the measurements is replaced by the next one in line by transferring the support 15, 37, 65 into the next measurement position Pj. In consequence the temperature sensor 99 is not exposed to temperature changes and can thus be used to reliably measure an integral temperature prevailing at the measurement site.

As an option, at least one additional temperature sensor 99, indicated by dotted lines in FIGS. 1, 4 and 6 can be foreseen, allowing for temperature compensations to be continued based on temperature measurements of one of the additional temperature sensors 99 in case the previously used one fails.

What is claimed is:

1. A measurement device for measuring a property of a fluid, including a concentration of a substance or an ion concentration in said fluid, comprising:

a housing including a housing section structured to be immersed into the fluid during a measurement operation;

an aperture disposed in a side wall surrounding an interior of said housing section or in a front wall closing off a front end of said housing section, the aperture configured for exposing a selected sensor for measuring said property of said fluid to said fluid, when said housing section is immersed into the fluid;

at least two sensors embodied for measuring said property of the fluid, each sensor including a distinct sensor contact separate from sensor contacts of other of the at least two sensors;

a movable mechanical support; and measurement electronics disposed within the movable mechanical support and electrically connected to a measurement contact disposed within the movable mechanical support, wherein:

each of said sensors is mounted in a different outside surface region of said movable mechanical support;

said movable mechanical support is movably secured inside said housing such that said movable mechanical support is transferable to multiple predefined measurement positions;

in each measurement position a different outside surface region of said movable mechanical support including one of said sensors is exposed to said aperture; and the selected sensor of the at least two sensors, which is exposed to said aperture, is connected to the measurement electronics via the sensor contact of the selected sensor and the measurement contact, which contacts the sensor contact of the selected sensor only when the movable mechanical support is transferred into the measurement position of the selected sensor.

2. The measurement device according to claim 1, wherein:

each of said sensors is located inside a recess in the corresponding outer surface region of said movable mechanical support, the recess having a depth dimensioned such that said sensor does not extend beyond a frontline defined by an outside surface of said movable mechanical support surrounding said recess.

3. The measurement device according to claim 1, wherein:

to enable said movable mechanical support to be transferred into said predefined measurement positions the movable mechanical support includes a manual ratcheting mechanism interlockingly engaging said movable mechanical support every time one of said measurement positions is reached, or a drive, including an electric motor or solenoid, wherein the drive moves said movable mechanical support from one measurement position into a consecutive measurement position each time it is activated, or a driven ratcheting mechanism, wherein the ratcheting mechanism transfers said movable mechanical support from one measurement position into a consecutive measurement position each time it is activated.

4. The measurement device according to claim 1, wherein:

said movable mechanical support includes a cylindrical section rotatably secured inside a cylindrical interior of said housing section by a retaining ring, allowing for said movable mechanical support to be transferred into said different measurement positions by rotating said cylindrical section around a longitudinal axis of the cylindrical section; and said sensors are arranged in a circle on outer surface regions of a front wall of said cylindrical section resting on said front wall of said housing section, wherein said aperture is in an off-centered position in said front wall corresponding to the positions of said sensors on said front wall of said movable mechanical support, or said sensors are arranged in a circle on outer surface regions of a cylindrical wall of said cylindrical section surrounded by said side wall of said housing section, wherein said aperture is in said side wall at a height corresponding to the height of said sensors on said cylindrical section of said support.

5. The measurement device according to claim 1, wherein:

said movable mechanical support includes a conveyor belt including two side sections extending in a direction essentially parallel to a longitudinal axis of said housing section along opposing inside surfaces of said housing section and one or two connecting sections connecting the two side sections;

said sensors are mounted on outside surface regions in recesses disposed in said outside surface regions, distributed along a length of said conveyor belt; and the movable mechanical support further includes a conveying means enabling the movable mechanical support to be transferred into said different measurement positions by conveying said conveyor belt, such that in each measurement position a different sensor located in one of said outside surface regions of said conveyor belt is exposed to said aperture.

6. The measurement device according to claim 5, wherein:

said aperture is located in said front wall of said housing section and said conveyor belt comprises an essentially flat region, larger than the size of said sensors, abutting on a flat inside surface of a front wall of said housing section surrounding said aperture, or said aperture is located in said side wall of said housing section and said conveyor belt comprises an essentially flat region, larger than the size of said sensors, abutting on a flat inside surface of said side wall of said housing section surrounding said aperture.

7. The measurement device according to claim 5, wherein:

said conveyor belt is mounted on a mounting frame supporting outer rims of said conveyor belt and equipped with bearings allowing for said conveyor belt to be rolled along the mounting frame.

8. The measurement device according to claim 5, wherein:

said conveyor belt forms a closed loop, comprising two side sections extending in a direction essentially parallel to the longitudinal axis of the housing section along opposing inside surfaces of said housing section and two connecting section connecting the two side sections completing the closed loop; and said conveying means allowing for the support to be transferred into the different measurement positions comprise:

an opening in said housing for exposing a section of said conveyor belt allowing for the conveyor belt to be conveyed manually, or conveying means comprising one or two toothed wheels comprising teeth successively engaging and disengaging into an outer rim of one of said connecting sections of said conveyor belt when said conveyor belt is conveyed forward, allowing for said conveyor belt to be conveyed manually or comprising a drive turning at least one of said toothed wheels to convey said conveyor belt from one measurement position into a consecutive measurement position each time it is activated.

9. The measurement device according to claim 5, wherein:
said conveying means allowing for the support to be transferred into said different measurement positions comprise a ratcheting mechanism engaging a section of said conveyor belt extending into a housing section adjacent to said housing section to be immersed into said fluid,
the ratcheting mechanism adapted to convey said conveyor belt forward by distance corresponding to a distance between consecutive sensors on said outer surface regions of said conveyor belt each time the ratcheting mechanism is activated, wherein said ratcheting mechanism is further adapted to be activated manually, via a lever or a push button, or via an electrical signal.

10. The measurement device according to claim 5, wherein:
said sensors comprise a mechanically rigid base and are mounted directly onto a surface of a recess in the respective outside surface regions of said conveyor belt; or
said sensors are mounted on mechanically rigid elements at the respective outside surface regions of said conveyor belt; or
a reinforcement reinforcing the sections of said conveyor belt comprising said sensors.

11. The measurement device according to claim 1, wherein:
said sensors are calibrated sensors, which were calibrated before the measurement device is put into measurement operation; and/or
said sensors are electrochemical sensors, including potentiometric or amperometric sensors, including an analyte sensitive membrane or a semiconductor-element.

12. The measurement device according to claim 1, wherein:
at least one temperature sensor embodied to measure a temperature prevailing at a measurement site, the temperature sensor located at or near said aperture and mounted independently of said movable mechanical support carrying said sensors; and
said temperature sensor is connected to the measurement electronics, which are further configured to perform temperature compensations of temperature dependent measurement errors of measurement results obtained by said sensors.

13. The measurement device according to claim 1, further comprising:
a seal between said aperture and an interior of said housing section, the seal provided by:
at least one surface of said movable mechanical support, including a surface of a cylindrical section or surfaces of sections of a conveyor belt of said movable mechanical support, surrounding said sensors, sealing by abutting on an inner surface of said housing section surrounding said aperture; or
a sealing element filling a gap between said movable mechanical support and said housing section and including an opening located adjacent to said aperture.

14. The measurement device according to claim 11, wherein:
said sensors are semiconductor-elements including an ion sensitive field effect transistor (ISFET) or a capacitor, whose capacitance depends on the concentration of the substance to be determined.

15. The measurement device according to claim 1, wherein:
each of the sensors includes a sensor module enabling the sensor to be powered and for measurement results of each sensor to be communicated wirelessly to the measurement electronics.

* * * * *